(12) United States Patent
Gopalan et al.

(10) Patent No.: US 10,094,788 B2
(45) Date of Patent: Oct. 9, 2018

(54) SURFACE ACOUSTIC WAVE SENSORS IN SEMICONDUCTOR PROCESSING EQUIPMENT

(71) Applicant: Applied Materials, Inc., Santa Clara, CA (US)

(72) Inventors: Ramesh Gopalan, Fremont, CA (US); Simon Yavelberg, Cupertino, CA (US); Zubin Huang, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 271 days.

(21) Appl. No.: 15/000,092

(22) Filed: Jan. 19, 2016

(65) Prior Publication Data
US 2017/0176349 A1    Jun. 22, 2017

Related U.S. Application Data

(60) Provisional application No. 62/270,254, filed on Dec. 21, 2015.

(51) Int. Cl.
| | | |
|---|---|---|
| *G01R 27/28* | (2006.01) | |
| *G01N 22/00* | (2006.01) | |
| *H01L 21/67* | (2006.01) | |
| *H01J 37/32* | (2006.01) | |

(52) U.S. Cl.
CPC ........ *G01N 22/00* (2013.01); *H01J 37/32935* (2013.01); *H01L 21/67253* (2013.01)

(58) Field of Classification Search
CPC .......................... G01N 22/00; H01L 21/67253
USPC ................................. 324/639, 637, 629, 600
See application file for complete search history.

(56) References Cited

U.S. PATENT DOCUMENTS

| | | | | |
|---|---|---|---|---|
| 6,005,916 A | * | 12/1999 | Johnson | A61B 5/05 378/87 |
| 7,391,372 B2 | * | 6/2008 | Lynch | H01L 24/18 343/700 MS |
| 7,453,184 B2 | * | 11/2008 | Kando | H03H 9/0222 310/313 B |
| 8,269,344 B2 | * | 9/2012 | Rofougaran | H01L 23/49816 257/728 |
| 8,587,482 B2 | * | 11/2013 | Liu | H01Q 1/2283 343/700 MS |

(Continued)

*Primary Examiner* — Tung X Nguyen
*Assistant Examiner* — Dominic Hawkins
(74) *Attorney, Agent, or Firm* — Patterson + Sheridan, LLP

(57) ABSTRACT

The implementations described herein generally relate to a sensing device for use in the semiconducting industry which sense process parameters to control semiconductor processes. More specifically, the implementations relate to packaging for a surface acoustic wave (SAW) based devices or wireless or RF-responsive sensors for use in the harsh processing environments of a semiconductor processing chamber such that the neither the sensor and its components nor the chamber components interfere with or contaminate one another. The sensor packaging may include various packaging layers with or without protective coatings and a waveguide. The packaging may have a thickness chosen such that the thickness is less than the electromagnetic wavelength of a SAW sensor radio wave. The sensing devices may be disposed in cavities of the chamber, the processing volume, on chamber components, and/or on the substrate.

20 Claims, 5 Drawing Sheets

(56) References Cited

U.S. PATENT DOCUMENTS

| | | | |
|---|---|---|---|
| 2003/0051366 A1* | 3/2003 | Ise | H01L 21/67253 34/58 |
| 2004/0185670 A1* | 9/2004 | Hamelin | C23C 16/4405 438/704 |
| 2005/0235917 A1* | 10/2005 | Fordemwalt | C23C 16/4407 118/723 R |
| 2007/0181255 A1* | 8/2007 | Hayasaka | C23C 16/455 156/345.33 |
| 2009/0180733 A1* | 7/2009 | Hwang | G02B 6/43 385/14 |

* cited by examiner

SURFACE ACOUSTIC WAVE SENSORS IN SEMICONDUCTOR PROCESSING EQUIPMENT

CROSS-REFERENCE TO RELATED APPLICATIONS

This application claims benefit of U.S. Provisional Patent Application Ser. No. 62/270,254, filed Dec. 21, 2015, the entirety of which is incorporated herein by reference.

BACKGROUND

Field

Implementations of the present disclosure generally relate to semiconductor processing and more specifically to an apparatus for deploying and monitoring a process using a sensing device in a semiconductor processing system.

Description of the Related Art

FIG. 1 (Prior Art) is a schematic cross sectional side view of a plasma process apparatus 100 used in FIG. 5 to describe various implementations. The plasma process apparatus in FIG. 1 is an inductively coupled plasma chamber and may be utilized alone or, as a processing module of an integrated semiconductor substrate processing system, or cluster tool, such as CENTURA® integrated semiconductor substrate processing system, available from Applied Materials, Inc. of Santa Clara, Calif.

As shown in FIG. 1 (Prior Art), the plasma process apparatus 100 may be a plasma process chamber 110 including a chamber body 130 and a chamber lid 120 that together define a processing volume 112. The plasma process chamber 110 may further include a substrate support 116 disposed in the processing volume 112, a plasma source assembly 160 disposed over the chamber lid 120, and a controller 140. The chamber body 130 may be coupled to an electrical ground 134. In some implementations, the substrate support 116 may be coupled, through a matching network 124, to a biasing power source 122.

The plasma source assembly 160 may include at least two RF coils, such as a first coil 109 and a second coil 111 surrounding the first coil 109. The first coil 109 and the second coil 111 may be concentric. An annular space 115 is defined between the first coil 109 and the second coil 111. The first coil 109 may be supported by two or more supports 162 and the second coil 111 may be supported by two or more supports 164. Supports 162, 164 may be made of a dielectric material and may be disposed on the chamber lid 120. Each coil 109, 111 may be coupled, through a matching network 119, to an RF power source 118.

The RF power source 118 may be capable of producing up to 13 W/cm$^2$ at a tunable frequency in a range from about 50 kHz to about 13.56 MHz. In some implementations, a power divider 104, such as a dividing capacitor, may be provided to control the relative quantity of RF power provided by the RF power source 118. The power divider 104 may be disposed in the line coupling the first coil 109 and the second coil 111 to the RF power source 118 for controlling the amount of RF power provided to each coil. In other implementations, each coil may be separately powered by a different RF source.

During operation, a substrate 114 may be placed on the substrate support 116 and process gases may be supplied from a gas panel 138 through entry ports 126 to form a gas mixture 150 within the processing volume 112. The gas mixture 150 may be transformed into a plasma 155 in the processing volume 112 by coupling RF power to the gas mixture from the first and second coils 109, 111 that are energized by the RF power source 118. The pressure within the processing volume 112 may be controlled using a throttle valve 127 and a vacuum pump 136. The temperature of the chamber body 130 may be controlled using liquid-containing conduits (not shown) that run through the chamber body 130. In one embodiment, helium gas from a gas source 148 may be provided via a gas conduit 149 to channels defined between the backside of the substrate 114 and grooves (not shown) disposed in the surface of the substrate support 116. The helium gas may be used to facilitate heat transfer between the substrate support 116 and the substrate 114.

The controller 140 may include a central processing unit (CPU) 144, a memory 142, and support circuits 146 for CPU 144 and may facilitate control of the components of the plasma process chamber 110 and, as such, of methods discussed herein. The controller 140 may be one of any form of general-purpose computer processor that can be used in an industrial setting for controlling various chambers and sub-processors. The memory 142, such as computer readable-medium, of the controller 140 may be one or more of readily available memory, such as random access memory (RAM), read only memory (ROM), floppy disk, hard disk, or any other form of digital storage, local or remote. The support circuits 146 are coupled to the CPU 144 for supporting the CPU 144 in any conventional manner. The circuits 146 may include cache, power supplies, clock circuits, input/output circuitry and sub-systems. The methods described herein may be stored in the memory 142 as software routine that may be executed or invoked to control the operation of the plasma process chamber 110 in the manner described herein.

The fabrication of integrated circuits in the semiconductor industry typically employs plasma to create and assist surface chemistry within a plasma reactor necessary to remove material from and deposit material to a substrate. In general, plasma is formed within the plasma reactor under vacuum conditions by heating electrons to energies sufficient to sustain ionizing collisions with a supplied process gas. Moreover, the heated electrons can have energy sufficient to sustain dissociative collisions and, therefore, a specific set of gases under predetermined conditions (e.g., chamber pressure, gas flow rate, etc.) are chosen to produce a population of charged species and chemically reactive species suitable to the particular process being performed within the chamber (e.g., etching processes where materials are removed from the substrate or deposition processes where materials are added to the substrate).

During, for example, an etch process, monitoring the plasma processing system can be essential when determining the state of a plasma processing system and determining the quality of devices being produced. Surface acoustic wave (SAW) based devices and sensors are advantageous for use in semiconductor processing equipment in that they are wireless and passive, requiring no battery, and may be placed in remote or hard to reach areas in the processing environment. However, SAW sensors are unable to withstand the harsh processing environments, which may include corrosive plasmas and RF energy inside the semiconducting processing chamber. Additionally, traditional SAW sensors include layers of lithium, niobium, or other elements not permitted in semiconductor processing equipment. Therefore, what is needed in the art is an apparatus for effectively packaging a SAW sensor for operation in a semiconductor processing chamber.

SUMMARY

The implementations described herein generally relate to a sensing device for use in the semiconducting industry, which sense process parameters to control semiconductor processes. More specifically, the implementations relate to packaging for a surface acoustic wave (SAW) based devices or wireless or RF-responsive sensors for use in the harsh processing environments of a semiconductor processing chamber such that the neither the sensor and its components nor the chamber components interfere with or contaminate one another. The sensor packaging may include various packaging layers with or without protective coatings and a waveguide. The packaging may have a thickness chosen such that the thickness is less than the electromagnetic wavelength of a SAW sensor radio wave. The sensing devices may be disposed in cavities of the chamber, the processing volume, on chamber components, and/or on the substrate.

In one embodiment, a wireless or radio-frequency responsive sensing device for use in a processing volume of a semiconductor process chamber is disclosed. The sensing device includes a transmitter and a receiver. The receiver is coupled to the semiconductor processing chamber and operable to communicate with the transmitter at a sensing frequency. The transmitter includes a first packaging layer, a second packaging layer contacting the first packaging layer, and a first antenna disposed between the first packaging layer and the second packaging layer. The transmitter also includes a sensor disposed between the first packaging layer and the second packaging layer, and a first waveguide embedded within the first packaging layer. The first waveguide includes a first filter to allow the sensing frequency to pass therethrough.

In another embodiment, a wireless or radio-frequency responsive sensing device is disclosed. The sensing device includes a transmitter and a receiver. The transmitter is coupled to at least one chamber component. The transmitter includes a first ceramic layer having a first face and a second face, the first face having a protective coating disposed thereon, a second ceramic layer having a third face and a fourth face, wherein the third face is opposite the fourth face, the second face contacts the third face, and the fourth face has a protective coating disposed thereon, and a first antenna disposed between the second face of the first ceramic layer and the third face of the second ceramic layer. The transmitter also includes a sensor disposed between the second face of the first ceramic layer and the third face of the second ceramic layer, and a first waveguide embedded within the first ceramic layer or the second ceramic layer. The receiver is operable to communicate with the transmitter at a sensing frequency. The receiver includes a third ceramic layer, a fourth ceramic layer contacting the third ceramic layer, and a second antenna disposed between the third ceramic layer and the fourth ceramic layer. The receiver also includes a second waveguide disposed between the third ceramic layer and the fourth ceramic layer, and a power source coupled to the receiver.

In yet another embodiment, a wireless or radio-responsive sensing device is disclosed. The sensing device includes a transmitter and a receiver. The transmitter is coupled to at least one chamber component and disposed inside a processing volume of a processing chamber. The transmitter includes a first ceramic layer, a second ceramic layer contacting the first ceramic layer, and a first antenna disposed between the first ceramic layer and the second ceramic layer. The transmitter also includes a sensor disposed between the first ceramic layer and the second ceramic layer, and a first waveguide comprising a metal material, wherein the first waveguide is embedded within the first ceramic layer or the second ceramic layer, and wherein the first waveguide comprises a first filter to allow a sensing frequency to pass therethrough. The receiver is disposed outside of the processing volume and is operable to communicate with the transmitter at the sensing frequency. The receiver includes a third ceramic layer, a fourth ceramic layer contacting the third ceramic layer, and a second antenna disposed between the third ceramic layer and the fourth ceramic layer. The receiver also includes a second waveguide disposed between the third ceramic layer and the fourth ceramic layer, wherein the second waveguide comprises a second filter to allow the sensing frequency to pass therethrough.

BRIEF DESCRIPTION OF THE DRAWINGS

So that the manner in which the above recited features of the present disclosure can be understood in detail, a more particular description of the disclosure, briefly summarized above, may be had by reference to implementations, some of which are illustrated in the appended drawings. It is to be noted, however, that the appended drawings illustrate only exemplary implementations and are therefore not to be considered limiting of its scope, may admit to other equally effective implementations.

Figure 1:
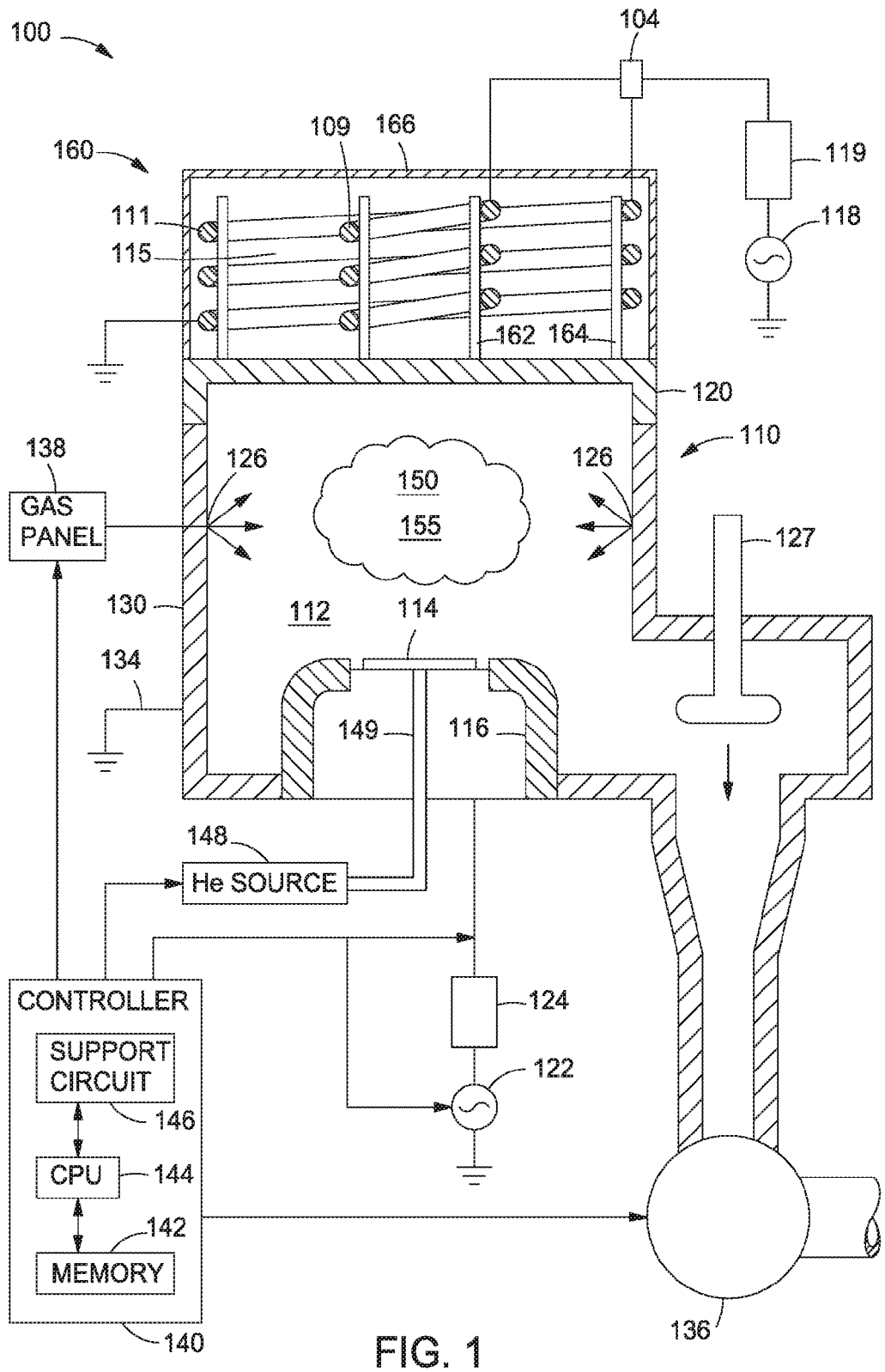
FIG. 1 (Prior Art) illustrates a schematic cross sectional view of a plasma processing apparatus used to describe implementations disclosed herein.

To facilitate understanding, identical reference numerals have been used, where possible, to designate identical elements that are common to the figures. It is contemplated that elements and features of one embodiment may be beneficially incorporated in other implementations without further recitation.

DETAILED DESCRIPTION

The implementations described herein generally relate to a sensing device for use in the semiconducting industry, which sense process parameters to control semiconductor processes. More specifically, the implementations relate to packaging for a surface acoustic wave (SAW) based devices or wireless or RF-responsive sensors for use in the harsh processing environments of a semiconductor processing chamber such that the neither the sensor and its components nor the chamber components interfere with or contaminate one another. The sensor packaging may include various packaging layers with or without protective coatings and a waveguide. The packaging may have a thickness chosen such that the thickness is less than the electromagnetic wavelength of a SAW sensor radio wave. The sensing devices may be disposed in cavities of the chamber, the processing volume, on chamber components, and/or on the substrate.

A "substrate" or "substrate surface," as described herein, generally refers to any substrate surface upon which processing is performed. For example, a substrate surface may include silicon, silicon oxide, doped silicon, silicon germanium, germanium, gallium arsenide, glass, sapphire, and any other materials, such as metals, metal nitrides, metal alloys, and other conductive or semi-conductive materials, depending on the application. A substrate or substrate surface may also include dielectric materials such as silicon dioxide, silicon nitride, organosilicates, and carbon dopes silicon oxide or nitride materials. The term "substrate" may further include the term "wafer." The substrate itself is not limited to any particular size or shape. Although the implementations described herein are made with generally made with reference to a round substrate, other shapes, such as polygonal, squared, rectangular, curved, or otherwise non-circular workpieces may be utilized according to the implementations described herein.

Figure 2:
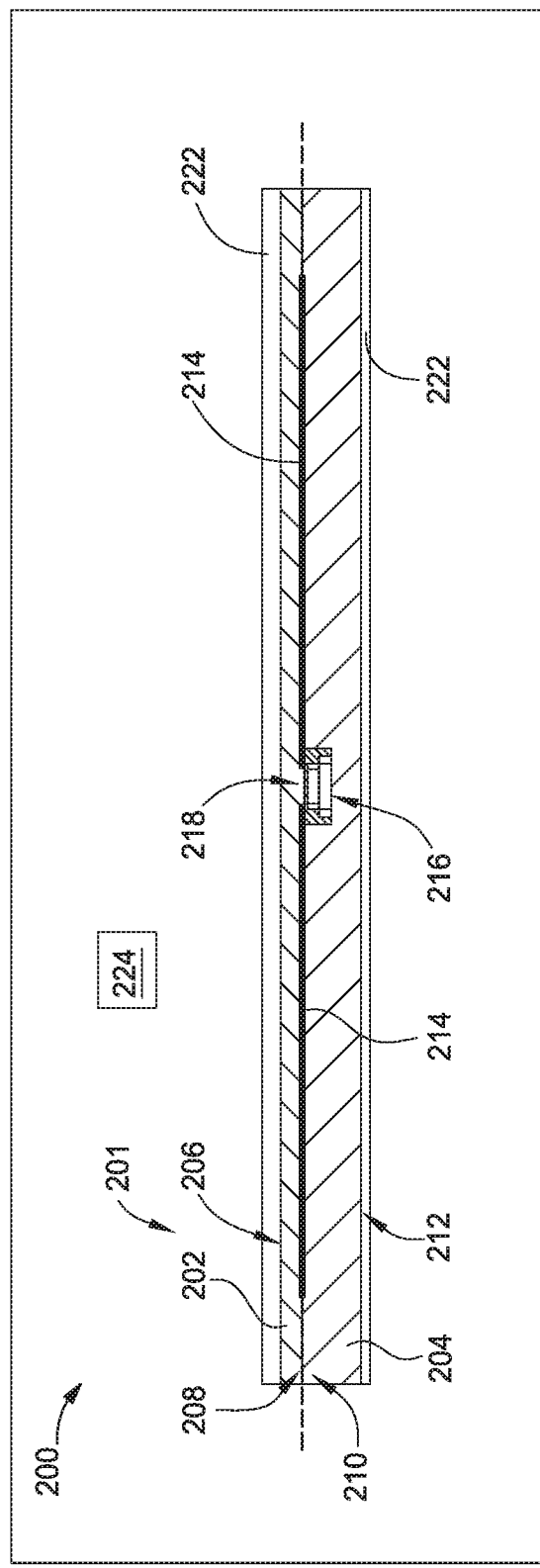
FIG. 2 illustrates a schematic side view of a sensing device, according to implementations described herein.

FIG. 2 illustrates a schematic side view of a sensing device 200 for use in the plasma process apparatus 100 of FIG. 1 (Prior Art). The sensing device 200 may be utilized within the plasma process apparatus 100, for example within the processing volume 112, and/or outside of the plasma process apparatus 100, for example adjacent the chamber lid 120. In some implementations, the sensing device may include a transmitter 201 and/or a receiver device 224. The sensing device may be a wireless and/or radio-responsive sensing device.

The transmitter 201 may comprise a first packaging layer 202 and/or a second packaging layer 204. The first packaging layer 202 and/or the second packaging layer 204 may comprise one of an alumina material, a ceramic material, a silica material, a quartz material, or combinations and mixtures thereof. In certain implementations, the first packaging layer 202 and/or the second packaging layer 204 may comprise a loose sintered ceramic material. The first packaging layer 202 and/or the second packaging layer 204 may each have a thickness, which is less than an electromagnetic skin depth of a radio wave of the sensing device 200. Overall, the transmitter 201 may have a thickness of about 200 microns or less, for example about 110 microns. In some implementations, the transmitter 201 may be wireless and/or batteryless.

The second packaging layer 204 may contact the first packaging layer 202. The first packaging layer 202 may have a first face 206 and a second face 208. The first face 206 may be opposite the second face 208. The second packaging layer 204 may have a third face 210 and a fourth face 212. The third face 210 may be opposite the fourth face 212. In some implementations, the third face 210 may contact the second face 208.

The transmitter 201 may further include a first antenna 214. The first antenna 214 may be disposed between the first packaging layer 202 and the second packaging layer 204. In certain implementations, the first antenna 214 may be disposed between the second face 208 of the first packaging layer 202 and the third face 210 of the second packaging layer 204. In some implementations, the first antenna 214 may be encased with the first packaging layer 202 and the second packaging layer 204 such that the first antenna 214 is not exposed outside of the first packaging layer 202 or the second packaging layer 204. The first antenna 214 may comprise a metal material, for example a copper material. Furthermore, the first antenna 214 may have a thickness of less than about 100 microns, for example less than about 65 microns. The first antenna 214 may transmit and/or receive signals to and from the transmitter 201 such that the transmitter 201 is in operative communication with a device, such as the receiver device 224, described infra.

The transmitter 201 may further include a sensor 216. The sensor 216 may be disposed between the first packaging layer 202 and the second packaging layer 204. In certain implementations, the sensor 216 may be disposed between the second face 208 of the first packaging layer 202 and the third face 210 of the second packaging layer 204. In some implementations, the sensor 216 may be encased with the first packaging layer 202 and the second packaging layer 204 such that the sensor 216 is not exposed outside of the first packaging layer 202 or the second packaging layer 204. The sensor 216 may detect and/or measure a physical property of a particular component, such as a chamber component or area of the plasma process apparatus 100. In some implementations, the sensor 216 may record, indicate, or otherwise respond to the detected or measured physical property. The sensor 216 may be in operative communication with the first antenna 214 such that upon receiving and/or detection of a particular physical property of a chamber component the sensor 216 signals the first antenna 214 to transmit or relay a signal to the receiver device 224. The signal transmitted or relayed by the first antenna 214 may be a radio wave. The first packaging layer 202 and the second packaging layer 204 may each have a thickness less than an electromagnetic skin depth of the radio wave sent by the transmitter 201.

The transmitter 201 may also include a first waveguide 218. In some implementations, the first waveguide 218 may be disposed and/or embedded within the first packaging layer 202 or the second packaging layer 204. In some implementations, the first waveguide 218 may be encased between the first packaging layer 202 and the second packaging layer 204 such that the first waveguide 218 is not exposed outside of the first packaging layer 202 or the second packaging layer 204. The first waveguide 218 may selectively admit only the sensing frequency to and from the transmitter 201, the receiver device 224, and/or the first antenna 214, while reflecting or absorbing other frequencies of electromagnetic energy. The first waveguide 218 may include a first filter designed to allow the sensing frequency to pass therethrough. In some embodiments, the first filter may be an aperture, iris, and/or post for filtering electromagnetic waves passing therethrough. In some implementations, the first waveguide 218 may be disposed between the first antenna 214 and the transmitter 201. In some implementations, the first waveguide 218 may confine or convey waves emitted from a component of the transmitter 201. The first waveguide 218 may be rectangular, cylindrical, or circular in shape, however it is contemplated that the first waveguide 218 may be of any suitable shape. In some implementations, the first waveguide 218 may be a slot. In some implementations, the first waveguide 218 may comprise a metal material.

In certain implementations, the transmitter 201 may also comprise a protective coating 222. The protective coating 222 may be disposed on or coupled to the first packaging layer 202 and or the second packaging layer 204. In some implementations, the protective coating 222 may be coupled to the first face 206 of the first packaging layer 202. In some implementations, the protective coating may be coupled to the fourth face of the second packaging layer 204. The protective coating 222 may comprise an yttria material, an yttria oxide material, an yttria fluoride material, among other suitable materials.

Figure 3:
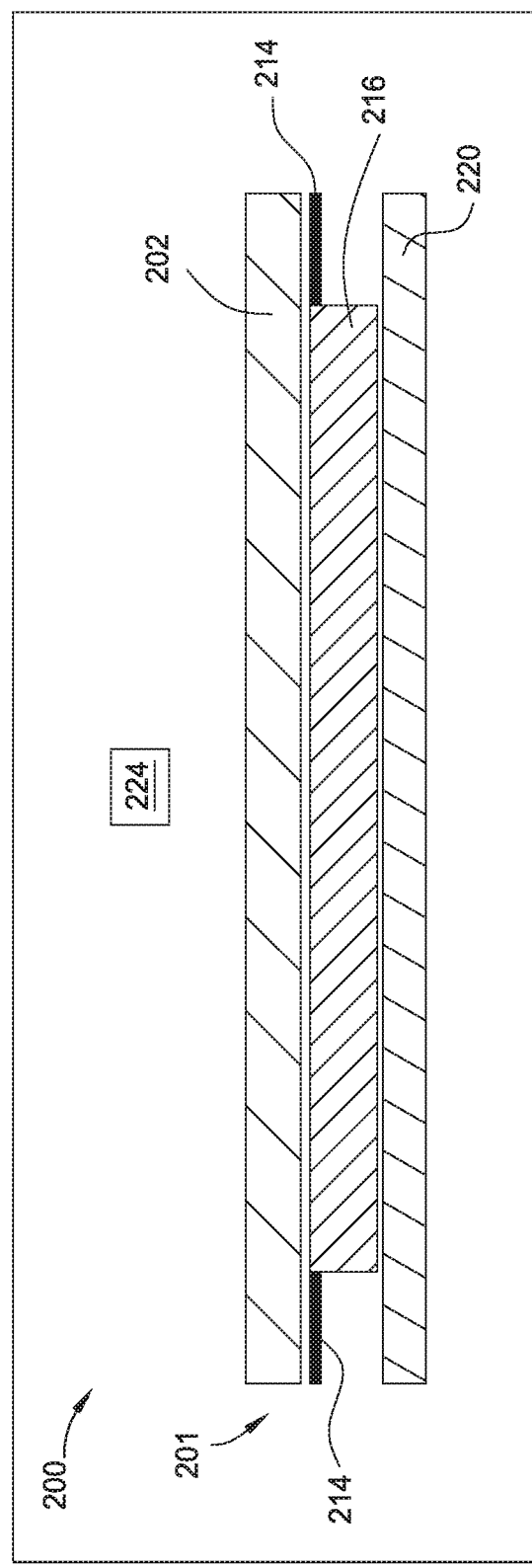
FIG. 3 illustrates a schematic side view of a sensing device, according to implementations described herein.

FIG. 3 schematically illustrates an alternate embodiment of the transmitter 201 of FIG. 2. As shown in FIG. 3, the second packaging layer 204 may comprise a ground plane 220. In some implementations, the ground plane 220 may be coupled to the second packaging layer 204. In some in implementations, the ground plane 220 may comprise the second packaging layer 204. The ground plane 220 may be fabricated from at least one of an anodized aluminum material, an aluminum material, a stainless steel material, a metal material with low permeability, a low paramagnetic metal material with a low magnetic moment, or mixtures and combinations thereof. In some implementations, the ground plane 220 may comprise an yttria material.

The transmitter 201 may transduce a radio signal to surface acoustic waves in a piezoelectric layer, which may provide a reply comprising a process parameter, such as a temperature reading, a pressure reading, or other information from a sensed volume. The transmitter 201 may transmit the information sensed to the receiver device 224.

Figure 4:
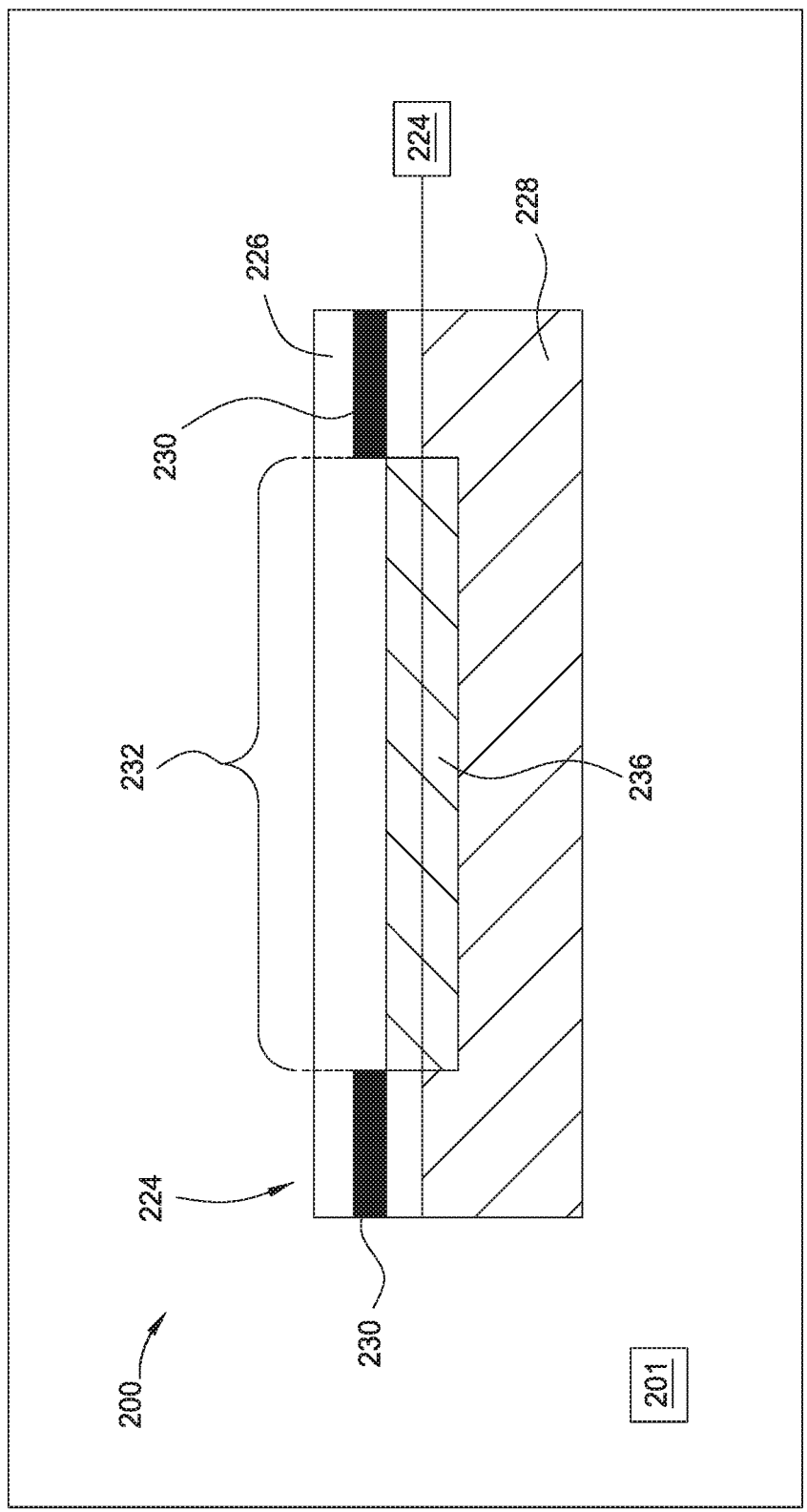
FIG. 4 illustrates a schematic side view of a sensing device, according to implementations described herein.

FIG. 4 illustrates a schematic side view of the sensing device 200 for use in the plasma process apparatus 100 of FIG. 1 (Prior Art). The sensing device 200 may further include a receiver device 224. The receiver device 224 may be operable to communicate with the sensor 216 and/or the first antenna 214 of the transmitter 201. In some implementations, and as shown in FIG. 2, the receiver device 224 may be coupled to the transmitter 201 via a wireless connection, such that the receiver device 224 is disposed a distance away from the sensor 216 or the first antenna 214 of the transmitter 201. In some implementations, the transmitter 201 may be located within the processing volume 112 of the plasma process apparatus 100 and/or coupled to a substrate 114 disposed within the processing volume 112, and the receiver device 224 may be disposed inside and/or outside of the processing volume 114 or the plasma process apparatus 100.

In certain implementations, in which the receiver device 224 is disposed inside the plasma process apparatus 100 or is coupled to a processing component of the plasma process apparatus 100, the receiver device 224 may include a third packaging layer 226 and a fourth packaging layer 228. The fourth packaging layer 228 may contact the third packaging layer 226 The receiver device 224 may also include a second antenna 230 and/or a receiver 236 disposed between the third packaging layer 226 and the fourth packaging layer 228, a second waveguide 232, and a power source 234 coupled to the receiver device 224.

The third packaging layer 226 and/or the fourth packaging layer 228 may comprise one of an alumina material, a ceramic material, a silica material, a quartz material, or combinations and mixtures thereof. In certain implementations, the third packaging layer 226 and/or the fourth packaging layer 228 may comprise a loose sintered ceramic material. The third packaging layer 226 and/or the fourth packaging layer 228 may each have a thickness, which is less than an electromagnetic skin depth of a radio wave of the transmitter 201.

In certain implementations, the second antenna 230 may be disposed between the third packaging layer 226 and the fourth packaging layer 228. In some implementations, the second antenna 230 may be encased with the third packaging layer 226 and the fourth packaging layer 228 such that the second antenna 230 is not exposed outside of the third packaging layer 226 or the fourth packaging layer 228. The second antenna 230 may comprise a metal material, for example a copper material. Furthermore, the second antenna 230 may have a thickness of less than about 100 microns, for example less than about 65 microns.

The receiver device 224 may further include a receiver 236. The receiver 236 may receive signals and/or information sent by the sensor 216 and/or the first antenna 214. The receiver 236 may be in operative communication with the second antenna 230. The third packaging layer 226 and the fourth packaging layer 228 may each have a thickness less than an electromagnetic skin depth of the radio wave sent by the transmitter 201.

The receiver device 224 may also include a second waveguide 232. In some implementations, the second waveguide 232 may be disposed and/or embedded within the third packaging layer 226 or the fourth packaging layer 228. In some implementations, the second waveguide 232 may be encased between the third packaging layer 226 and the fourth packaging layer 228 such that the second waveguide 232 is not exposed outside of the third packaging layer 226 or the fourth packaging layer 228. The second waveguide 232 may selectively admit only the sensing frequency to and from the transmitter 201, the receiver 224, the first antenna 214, and/or the second antenna 230, while reflecting or absorbing other frequencies of electromagnetic energy. In some implementations, the second waveguide 232 may selectively reflect and/or enhance the electromagnetic field intensity of the sensing frequency in the vicinity of the sensing device 200. The second waveguide 232 may include a second filter designed to allow the sensing frequency to pass therethrough. In some embodiments, the second filter may be an aperture, iris, and/or post for filtering electromagnetic waves passing therethrough. In some implementations, the second waveguide 232 may be disposed between the second antenna 230 and the receiver device 224. In some implementations, the second waveguide 232 may confine or convey waves emitted from a component of the sensing device 200. The second waveguide 232 may be rectangular, cylindrical, or circular in shape, however it is contemplated that the second waveguide 232 may be of any suitable shape. In some implementations, the second waveguide 232 may be a slot. In some implementations, the second waveguide 232 may comprise a metal material. In certain implementations, the ground plane 220 may include the second waveguide 232.

In some implementations, the transmitter 201 and/or the receiver device 224 of the sensing device 200 may each further comprise an RF filter, as processing chambers include high power RF sources (e.g., 13.56 MHz). In certain implementations, the RF filter may be a high-pass RF filter. For example, a high-pass filter may protect a 2.4 GHz sensor from interference from a 13.56 MHz chamber source power.

Figure 5:
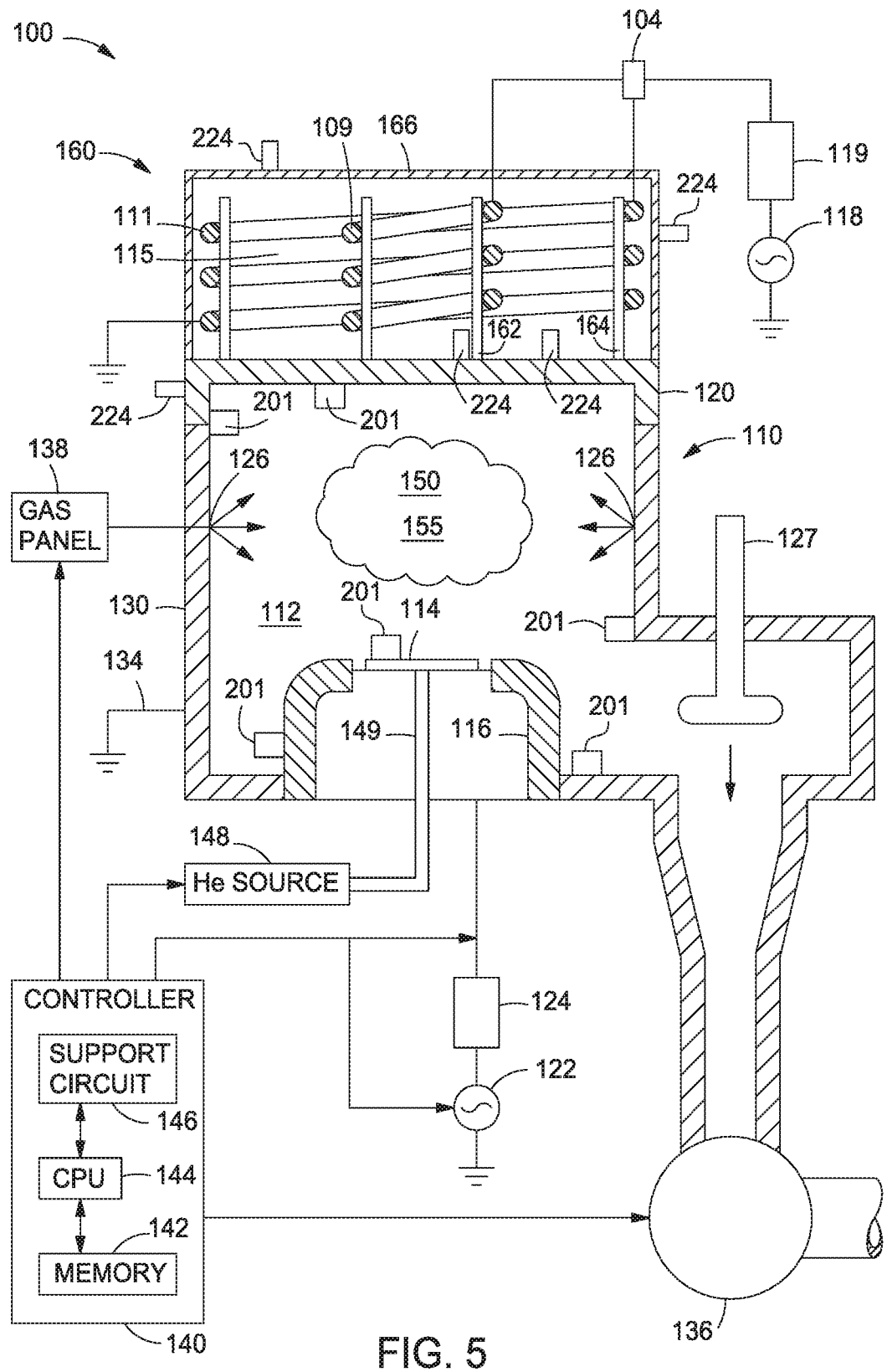
FIG. 5 illustrates a schematic cross section view of the plasma processing apparatus of FIG. 1 (Prior Art) with a sensing device of FIGS. 2-4 disposed therein, according to various implementations described herein.

FIG. 5 schematically illustrates placement locations of the transmitter 201 of the sensing device 200 within the processing volume 112 of the plasma process apparatus 100 of FIG. 1. The sensing device 200 may operate in wired and/or wireless communication. As such, the transmitter 201 may be in operative communication with the receiver device 224. As shown, one or more transmitters 201 may be disposed within the processing volume 112. In some implementations, the transmitter 201 may be coupled to the chamber body 130, the chamber lid 120, a chamber component (for example, an upper chamber liner, a lower liner, an ESC, an ESC cooling pad, a plasma screen, among other locations), and/or the substrate 114. In certain implementations, the fourth face 212 of the second packaging layer 204 may be coupled to the chamber body 130, the chamber lid 120, and/or the substrate 114. Furthermore, FIG. 5 further illustrates placement locations of the receiver device 224. As shown, the receiver device 224 may be disposed inside the processing volume 112 and/or outside of the processing volume 112. In some implementations, the receiver device 224 may be coupled to at least one chamber component. In some implementations, the receiver device 224 may be disposed above the chamber lid 120 outside of the processing volume 112.

Additionally, the transmitter 201 of the sensing device 200 may be disposed in cavities in ceramic plates within the processing volume 112. In some implementations, the cavity may have a metallic sealing on an outside edge of the ceramic plate with a thin dielectric. In some implementations, there may be no metal within the line of sight between the transmitter 201 and the receiver device 224. However, as numerous commercial processing chambers are enclosed by metal, openings that are comparable to the sensing wavelength may be utilized to access the transmitter 201 and/or the receiver device 224. By way of example only, and as discussed supra, in an etch chamber the receiver device 224 may be disposed above the chamber lid 120 and outside of the processing volume 112, thus allowing access to the transmitters 201 placed at any location within the processing volume 112.

The transmitter 201 and the receiver device 224 may be in operative communication via a wired and/or wireless connection. In some examples, a wireless connection may be utilized, and this wireless connection may occur at a specific sensing frequency or frequency band that is different from the frequency of any other electromagnetic energy supplied to the processing chamber or its vicinity.

Benefits of the present disclosure include added sensing capability (for example, temperature sensing, pressure sensing, layer stress sensing, etc.) to semiconductor processing equipment. The sensing device disclosed may sense process parameters to better control desired semiconductor processes without interfering with the processing environment.

Furthermore, testing was performed and results indicated that the sensing device disclosed is protected from the harsh plasma and processing conditions of an etching chamber due to the protective packaging and/or coatings disposed on the protective packaging. Additionally, the processing chamber is protected from the contaminants disposed and/or contained within the sensing device, as the contaminants have not been shown to leak therefrom. The protective coatings disposed on the outside of the transmitter and receiver device of the sensing device have also been shown to protect the sensing device from the harsh processing conditions, plasmas, and aggressive environments often encountered in semiconductor manufacturing.

Additional benefits include that the transmitter and/or received devices of the sensing device disclosed may be disposed at any location within the processing chamber. For example, any inner surface of the processing chamber with a line of sight to the substrate may be utilized for coupling a sensing device therewith. Furthermore, the thickness of the sensing device has been shown to allow specific radio waves to penetrate therethrough. As such, specific SAW frequencies are permitted to transmit to and/or from the sensing device, while keeping out other unwanted frequencies. The packaging of the sensing device disclosed blocks and filters processing frequencies, however allows desired frequencies to penetrate therethrough.

In summation, implementations described herein provide a sensing device for use in the semiconducting industry, which sense process parameters to control semiconductor processes. More specifically, the implementations relate to packaging for a surface acoustic wave (SAW) based devices or wireless or RF-responsive sensors for use in the harsh processing environments of a semiconductor processing chamber such that the neither the sensor and its components nor the chamber components interfere with or contaminate one another. The sensor packaging may include various packaging layers with or without protective coatings and a waveguide. The packaging may have a thickness chosen such that the thickness is less than the electromagnetic wavelength of a SAW sensor radio wave. The sensing devices may be disposed in cavities of the chamber, the processing volume, on chamber components, and/or on the substrate.

While the foregoing is directed to implementations of the present disclosure, other and further implementations of the disclosure may be devised without departing from the basic scope thereof, and the scope thereof is determined by the claims that follow.

What is claimed is:

1. A wireless or radio-frequency responsive sensing device, comprising:
   a transmitter for use in a processing volume of a semiconductor processing chamber, the transmitter comprising:
   a first packaging layer;
   a second packaging layer contacting the first packaging layer;
   a first antenna disposed between the first packaging layer and the second packaging layer;
   a sensor disposed between the first packaging layer and the second packaging layer; and
   a first waveguide embedded within the first packaging layer, wherein the first waveguide comprises a first filter to allow a sensing frequency to pass therethrough; and
   a receiver coupled to the semiconductor processing chamber and operable to communicate with the transmitter at the sensing frequency, the receiver comprising:
   a second waveguide in the receiver, wherein the second waveguide comprises a second filter to allow the sensing frequency to pass therethrough.

2. The sensing device of claim 1, wherein the first packaging layer comprises one of an alumina material, a ceramic material, a silica material, or a quartz material.

3. The sensing device of claim 1, wherein the second packaging layer is disposed on a substrate.

4. The sensing device of claim 1, wherein the second packaging layer is disposed on a chamber component of the semiconductor processing chamber.

5. The sensing device of claim 1, wherein the first waveguide comprises a metal material.

6. The sensing device of claim 1, wherein the second packaging layer comprises a ground plane, wherein the ground plane is fabricated from at least one of an anodized aluminum material, an aluminum material, a stainless steel material, a metal material with low permeability, and a low paramagnetic metal material with a low magnetic moment.

7. The sensing device of claim 1, wherein the first antenna comprises a copper material.

8. The sensing device of claim 1, wherein the first antenna has a thickness of less than about 65 microns.

9. The sensing device of claim 1, wherein the sensing device has a thickness of less than about 110 microns.

10. The sensing device of claim 1 further comprising:
    a protective coating disposed on the first packaging layer and the second packaging layer.

11. The sensing device of claim 10, wherein the protective coating comprises an yttria material, an yttria oxide material, or an yttrium fluoride material.

12. The sensing device of claim 1, wherein the first packaging layer and the second packaging layer each have a thickness less than an electromagnetic skin depth of the sensing frequency of a radio wave of the sensing device.

13. The sensing device of claim 1, wherein the transmitter and the receiver are in operative communication via a wireless connection.

14. A wireless or radio-frequency responsive sensing device, comprising:
 a transmitter coupled to at least one chamber component, the transmitter comprising:
  a first ceramic layer having a first face and a second face, the first face having a protective coating disposed thereon;
  a second ceramic layer having a third face and a fourth face, wherein the third face is opposite the fourth face, the second face contacts the third face, and the fourth face has a protective coating disposed thereon;
  a first antenna disposed between the second face of the first ceramic layer and the third face of the second ceramic layer;
  a sensor disposed between the second face of the first ceramic layer and the third face of the second ceramic layer; and
  a first waveguide embedded within the first ceramic layer or the second ceramic layer; and
 a receiver operable to communicate with the transmitter at a sensing frequency, the receiver comprising:
  a third ceramic layer;
  a fourth ceramic layer contacting the third ceramic layer;
  a second antenna disposed between the third ceramic layer and the fourth ceramic layer; and
  a second waveguide disposed between the third ceramic layer and the fourth ceramic layer.

15. The sensing device of claim 14, wherein the receiver is coupled to a semiconductor processing chamber.

16. The sensing device of claim 15, wherein the receiver is disposed outside of a processing volume of the semiconductor processing chamber.

17. The sensing device of claim 14, wherein the first waveguide comprises a first filter to allow the sensing frequency to pass therethrough.

18. The sensing device of claim 14, wherein the second waveguide comprises a second filter to allow the sensing frequency to pass therethrough.

19. A wireless or radio-responsive sensing device, comprising:
 a transmitter coupled to at least one chamber component and disposed inside a processing volume of a processing chamber, the transmitter comprising:
  a first ceramic layer;
  a second ceramic layer contacting the first ceramic layer;
  a first antenna disposed between the first ceramic layer and the second ceramic layer;
  a sensor disposed between the first ceramic layer and the second ceramic layer; and
  a first waveguide comprising a metal material, wherein the first waveguide is embedded within the first ceramic layer or the second ceramic layer, and wherein the first waveguide comprises a first filter to allow a sensing frequency to pass therethrough; and
 a receiver disposed outside of the processing volume, wherein the receiver is operable to communicate with the transmitter at the sensing frequency, the receiver comprising:
  a third ceramic layer;
  a fourth ceramic layer contacting the third ceramic layer;
  a second antenna disposed between the third ceramic layer and the fourth ceramic layer; and
  a second waveguide disposed between the third ceramic layer and the fourth ceramic layer, wherein the second waveguide comprises a second filter to allow the sensing frequency to pass therethrough.

20. The sensing device of claim 19, further comprising:
 a protective coating disposed on the first ceramic layer and the second ceramic layer, wherein the protective coating comprises an yttria material, an yttria oxide material, or an yttrium fluoride material.

* * * * *